United States Patent [19] [11] 3,980,662
Watanabe et al. [45] Sept. 14, 1976

[54] PROCESS FOR PREPARING ACID AMIDES

[75] Inventors: Yoshihiro Watanabe, Takatsuki; Takeshi Yamahara, Itami; Shun Inokuma; Tooru Tokumaru, both of Takatsuki, all of Japan

[73] Assignee: Sumitomo Chemical Company, Limited, Osaka, Japan

[22] Filed: June 12, 1974

[21] Appl. No.: 478,613

[30] Foreign Application Priority Data
June 19, 1973 Japan.............................. 48-69555
July 28, 1973 Japan.............................. 48-85222
Aug. 3, 1973 Japan.............................. 48-87891

[52] U.S. Cl. .................. 260/295.5 A; 260/557 R; 260/558 R; 260/561 B; 260/561 HL; 260/561 K; 260/561 N; 260/561 R; 252/431 N
[51] Int. Cl.² .............. C07D 213/82; C07C 102/08
[58] Field of Search............... 260/295.5 A, 561 N, 260/561 R, 558 R, 561 B, 561 HL, 557 R, 561 K

[56] References Cited

UNITED STATES PATENTS
3,381,034  4/1968  Greene et al. ................. 260/561 N
3,674,848  7/1972  Schoenbrunn et al. ......... 260/558 R OTHER PUBLICATIONS
Calmon et al., Ion Exchangers in Organic and Biochemistry, New York-Interscience Publishers (1957), pp. 22–28, 662–666.

Primary Examiner—Natalie Trousof
Assistant Examiner—Bernard Dentz
Attorney, Agent, or Firm—Stewart and Kolasch, Ltd.

[57] ABSTRACT

The acid amides are produced by a process comprising hydrating a nitrile compound in the presence of a copper-containing polymer having basic nitrogenous groups in the polymer chain or linked with the polymer chain as a catalyst.

17 Claims, No Drawings

PROCESS FOR PREPARING ACID AMIDES

The present invention relates to a process for preparing acid amides. More particularly, it relates to a process for preparing acid amides by hydrating a nitrile compound in the presence of a catalyst which comprises using as a catalyst a copper-containing polymer obtained by contacting a copper salt or a copper complex having replaceable ligands with a polymerized material having basic nitrogenous groups in the polymer chain or linked therewith.

The hydration of nitrile compounds is a well known method for preparing carboxamides. Especially, the hydration of acrylonitrile is widely applied to produce acrylamide on an industrial scale. The hydration reaction is also of great significance to produce various intermediates useful for organic synthesis.

Hitherto, the hydration of nitrile compound has been effected in the presence of a strong mineral acid. Thus, this process requires the use of an alkali in a large amount for the neutralization of the mineral acid after the hydration is completed, thereby producing a large amount of by-products. For example, where sulfuric acid is used for preparing an unsaturated amide such as acrylamide or methacrylamide by hydrating the corresponding nitrile compound, an alkali is used industrially in a great amount to neutralize the reaction mixture, resulting in the formation of by-products such as ammonium sulfate. The large by-production gives rise to troublesome operations for handling and also causes economic disadvantages. Therefore, it has been desired to provide a process where an acid is unnecessary as a catalyst, thereby being capable of obviating by-production caused by the use of the acid.

An improved process has been proposed where a copper catalyst such as metallic copper or copper oxide is used. This process is said to be unsatisfactory because the catalyst to be used therein has some points necessary to be improved with respect to a process for the preparation and the quality of the catalyst. Furthermore, the use of the metallic copper such as Raney copper or hydrogen-reduced copper has some disadvantages that the activity thereof is reduced immediately upon exposure to air and at the same time harmful conditions will be induced by burning the catalyst.

In order to obviate the disadvantages of said conventional catalysts, the present inventors have made extensive studies on a variety of copper compounds which may be used as a catalyst for the hydration of a nitrile compound. As a result, it has been found that a copper-containing polymer obtained by contacting a copper salt or a copper complex having a replaceable ligand with a polymerized material having a basic nitrogenous group in the polymer chain or linked therewith is effective as the catalyst for the hydration of not only acrylonitrile and methacrylonitrile but also any other nitrile compound. It has also been found that the copper-containing polymer is produced by polymerizing a vinyl monomer containing a copper salt or a copper complex having a basic nitrogenous group bonded to the copper atom as a ligand.

The object of the present invention is to provide a process for the preparation of carboxamides by the hydration of the corresponding nitrile compounds. It is another object of the present invention to provide a process for preparing carboxamides by hydrating the nitrile compounds in the presence of a copper-containing polymer obtained by contacting a copper salt or a copper complex having a replaceable ligand with a polymerized material having a basic nitrogenous group in the polymer chain or linked therewith or by polymerizing a vinyl monomer containing a copper salt or a copper complex having a basic nitrogenous group bonded to the copper atom as a ligand. Other objects, features and advantages of the present invention will become apparent during the course of the following description. The acid amides of the present invention such as, for example, acrylamide or methacrylamide are useful as intermediates for manufacturing various adhesives, agents for strengthening paper, water improving agents or the like.

The polymerized material containing a basic nitrogenous group is intended to mean a polymer which possesses in the polymer chain or linked therewith the basic nitrogenous group. The polymerized material may be prepared by the polymerization of a monomer containing a basic nitrogenous group therein or by the introduction of a basic nitrogenous group into the main or side chain of an appropriate polymerized material. The polymerized material to be used in the present invention includes a homopolymer, a copolymer or a mixture thereof. The monomer to be preferably used for this purpose includes a vinyl monomer such as N,N-dimethylaminoethyl methacrylate, 4-vinylpyridine, 2-vinylpyridine or the like. The polymerized material capable of forming a copper-containing polymer by contacting it with a copper salt or a complex thereof includes a homopolymer, a copolymer and a mixture thereof of 2-vinylpyridine, 4-vinylpyridine, N,N-diethylaminomethylmethacrylate, N,N-dimethylaminoethylacrylate, vinyl-N,N-diethylaminoacetate, ethyleneimine or the like. Examples of the homopolymer thereof are poly(2-vinylpyridine), poly(N,N-diethylaminoethylmethacrylate), poly(N,N-dimethylaminoethylmethacrylate), poly(vinyl-N,N-diethylaminoacetate), polyethyleneimine, poly(2-methyl-4-vinylpyridine), poly(2-n-butyl-4-vinylpyridine) or the like. Examples of the copolymers thereof are styrene-2-vinylpyridine copolymer, styrene-4-vinylpyridine copolymer, styrene-N,N-dimethylaminoethylmethacrylate copolymer, styrene-N,N-diethylaminoethylmethacrylate copolymer, vinyltoluene-2-vinylpyridine copolymer, vinyltoluene-4-vinylpyridine copolymer, styrene-vinylisoquinoline copolymer or the like. There may also be included herein a polymerized material prepared by the copolymerization of such illustrative polymers with a cross-linking agent such as divinylbenzene, divinylphthalate, ethylene glycol diacrylate or the like.

The basic nitrogenous group to be present in the polymerized material means a nitrogenous group in which at least one nitrogen atom thereof possesses an electron pair capable of forming a coordination bond with a copper atom. Examples of such basic nitrogenous groups are a primary amine ($-NH_2$), a secondary amine ($-NH-$), a tertiary amine ($=N-$), an imine ($=C=NR$) or an oxime ($=C=N-OH$) and an atomic group having a heterocyclic structure containing the basic nitrogen atom such as pyridine, imidazole, quinoline, adenine, cytosine, oxazole or the like.

The catalyst of the present invention is prepared by contacting the basic nitrogenous group of the polymerized material with a copper atom. More particularly, the copper-containing polymer catalyst according to the present invention is prepared by reacting the polymerized material having in the polymer chain or linked therewith the basic nitrogenous group with a copper salt or a copper complex having a replaceable ligand. The copper salt to be used herein includes copper salt of an inorganic acid and an organic acid. Examples of the former are copper chloride, copper bromide, copper iodide, copper sulfate, copper nitrate or the like. Examples of the latter are copper formate, copper acetate, copper propoinate, copper oxalate, copper tartrate or the like. The copper salt of an organic acid is preferred. The copper complex to be used herein includes a basic nitrogenous group-containing copper complex such as copper chloride-pyridine complex, a phosphorus-containing copper complex such as copper formate-triphenylphosphine complex, a sulfur-containing copper complex such as copper chloride - dimethyl-sulfide, or the like. The reaction of the polymerized material with the copper compound may be carried out by dissolving the copper salt or the complex thereof in an appropriate solvent and contacting it with the polymerized material. This reaction usually proceeds readily. The copper-containing polymer may be prepared by evaporating the solvent or by re-precipitating the product with ether or a saturated hydrocarbon. The former procedure may give a polymer in the form of a film or in other forms, and the latter may give a polymer in the form of powders and having a large surface area. For example, the addition of a solution of a copper salt or a copper complex in ethanol to a solution of the polymerized material in a solvent, e.g., to a solution of poly(4-vinylpyridine) in ethanol or in N,N-dimethylformamide may give a reaction product which precipitates as a complex. Where the polymerized material is insoluble in a solvent, the catalyst may be prepared by dissolving the copper salt or the copper complex in a solvent, adding thereto the polymerized material to bring it in good contact with the copper salt or the complex thereof, filtering and washing the product. An alternative process for preparing the catalyst is to polymerize a vinyl monomer containing the copper salt or the copper complex having the basic nitrogenous group bonded to the copper atom as a ligand. The polymerizable monomer possessing the basic nitrogenous group as a ligand includes a vinyl monomer such as, for example, vinylpyridines or derivatives thereof. A monomer copolymerizable with the vinyl monomer may contain a basic nitrogenous group. The polymerization may be effected in the presence of an initiator such as a peroxide or ABIN.

The atomic ratio of the copper atom (Cu) to the basic nitrogen atom (N) of the catalyst may be not more than one (Cu/N ≦ 1.0) and may be adjusted depending upon the amount of the polymerized material, the structure of the polymerized material having the basic nitrogenous atom, the particle size of the polymerized material, the kind of solvent and the concentration of the copper salt or copper complex in the solvent.

Although the catalyst of the present invention is effective per se, the catalytic activity may be increased by heat treatment. The heat treatment may be generally effected in an inert gas such as nitrogen or a gaseous hydrogen atmosphere in order to prevent a decrease in the catalytic activity which will be otherwise exerted by the influence of gaseous oxygen. The heat treatment may be in some cases carried out while pumping out the air by means of a vacuum pump. Studies on magnetic, x-ray and elementary analyses reveal that a part of the copper atom in the catalyst which was heat treated is converted to the zero-valence or the monovalence.

A time during which heat treatment is effected may be appropriately selected depending upon the heat resistance of the polymer and the kind of the copper salt to be used. The suitable temperature of heat treatment may be from about 50 to 400° C., more preferably from about 80° to 200°C.

The catalyst thus obtained is in the form of beads or powders. Although the catalyst may be used per se, it may be in some cases used in a form in which the catalyst is adjusted to have an appropriate particle size by means of a compression molding method. The catalyst may also be employed together with a carrier which is applicable to conventional catalysts for the hydration of a nitrile compound.

The catalyst of the present invention exhibits some specific properties as compared with copper catalysts prepared by conventional procedures so that widely practical applications to a variety of fields other than the hydration of nitriles are to be expected, too. Since the copper atom in the catalyst is coordinated or dispersed in an atomic state with respect to the basic nitrogen atom, the catalytic activity thereof and the efficiency of the copper atom per unit weight are shown to be extremely high. Furthermore, as compared with the sole use of a copper metal catalyst, the copper atom present in the catalyst of the present invention may give the interesting effect, together with the synergistic effect of the copper atom with the basic nitrogenous group, that an electronic influence over the compound to be reacted is exerted by means of the coexisting effect of the field provided by the basic nitrogenous group present in the catalyst.

The catalyst of the present invention does not ignite after being exposed to the air and is so stable that it can be handled in the air although it is preferred to handle and store it in an inert gas in order to maintain the catalytic activity thereof effectively.

It is said to be unexpected that the catalyst of the present invention hydrates a nitrile group in a nitrile compound selectively without generally exerting any great influence over the other parts thereof. It is also said to be unexpected that it hardly acts on the acid amide group which is converted from the nitrile group. These characteristics of the catalyst of the present invention make it possible to have the hydration reaction accomplished generally with an extremely high selectivity. These features are supposed to come from the effects attributable to the electronic field of the basic nitrogenous group remaining in the catalyst and to the copper atom in an atomic state exerting a mutual action together with the nitrogen atom. These properties which are supposed to serve to provide the catalyst of the present invention with an extremely high activity and selectivity are not provided by conventional simple copper catalysts.

The hydration reaction of a nitrile compound according to the present invention may be carried out under relatively mild conditions at a temperature of from about 10° to 300° C. The reaction temperature of from about 10° to 200° C. is preferable to maintain the reaction at an appropriate rate. The reaction may be carried out by the use of water in an amount less than the stoichiometric amount to the nitrile compound. However, it is preferred to use water in an amount from about 1.5 to 50 times more than the stoichiometric amount thereof. An inert solvent such as, for example, methanol, ethanol, tetrahydrofuran, dioxane or N,N-dimethylformamide may be used together with water. The reaction may be carried out in either the gaseous or liquid phase, the liquid phase being preferred. Where the liquid phase is applied, the use of a solvent such as methanol or the like may serve to decrease the amount of water to be otherwise used and produce the carboxamide aqueous solution in high concentrations by carrying out the reaction in a homogeneous liquid phase and removing the solvent to be used from the reaction mixture.

The reaction of the present invention is applicable to any compound having at least one nitrile group including an aliphatic nitrile compound, an aromatic nitrile compound or the like. There may be included, for example, an alkyl nitrile having an alkyl group of one to ten carbon atoms, preferably of one to eight carbon atoms, such as acetonitrile, propionitrile, butyronitrile or the like, a substituted alkylnitrile in which said alkylnitrile is substituted by an appropriate substituent, such as methoxyacetonitrile or the like, an alkenylnitrile having an alkenyl group of two or ten carbon atoms, preferably two to eight carbon atoms, such as acrylonitrile, methacrylonitrile, ethacrylonitrile, crotononitrile or the like, a halogen substituted alkenylnitrile in which said alkenylnitrile is substituted by a halogen atom, such as α-chloroacrylonitrile, α-bromoacrylonitrile or the like, a cycloalkylnitrile having a cycloalkyl group with three to eight carbon atoms such as cyclopentanonitrile, cyclohexanecarbonitrile or the like, an aralkylnitrile such as benzyl cyanide, cinnamonitrile, α-naphthylacetonitrile or the like, an arylnitrile such as benzonitrile, naphthonitrile, nicotinonitrile or the like, a polynitrile such as oxalonitrile, malononitrile, succinonitrile, sebaconitrile, maleonitrile, cyclobutane 1,2-dicyanide, phthalonitrile, glutaronitrile, adiponitrile, pimelonitrile, suberonitrile or the like and other types of nitriles such as benzoyl cyanide, acetyl cyanide or the like.

The copper atom present in the catalyst of the present invention is dispersed in such an atomic state that it is under a condition under which the catalyst activity thereof is readily exerted. There are some cases where the copper atom thereof is oxidized in the reaction system and eluted as a cupric ion ($Cu^{++}$), thus lowering the catalytic activity with the reaction time. The presence of the cupric ion may also cause the coloring of a product. Accordingly, it is necessary to prevent the copper ion from being eluted into the reaction system. The addition of metallic zinc to the reaction system is so effective that the elution of the copper atom is prevented without lowering the activity of the copper catalyst to a significant extent and the catalytic activity thereof is maintained. The metallic zinc is preferably used in the form of powders having a size of less than 20 mesh. The amount of the metallic zinc to be used is from about 0.001 to 200 percent by weight of the catalyst, preferably from about 0.1 to 50 percent by weight.

The amount of the catalyst to be used herein may vary depending upon the manner in which the reaction is carried out or the type thereof. In view of the catalyst of the present invention it is particularly suited for the reaction in the liquid phase. When a suspension procedure is applied, the amount of the catalyst is usually about 0.1 percent by weight or more, preferably from about 0.1 to 100 percent by weight of the starting reaction medium. Although the suspension procedure is advantageously applicable, it is also convenient to employ a fixed bed procedure. In the fixed bed procedure, the amount of the catalyst may vary depending upon the reaction temperature and the concentration of the nitrile compound, and the space velocity therein may be usually about 0.1 to 100 hour$^{-1}$, preferably from about 1 to 50 hour$^{-1}$.

The reaction of the present invention proceeds rapidly with an extremely high selectivity to afford a carboxamide in high yields.

The following examples illustrate the present invention without, however, limiting the same thereto. The words "part" or "parts" in the following examples mean a part or parts by weight, respectively.

EXAMPLE 1

To a suspension of 4-vinylpyridine (80 parts) and divinylbenzene (7.6 parts) in water (320 parts) were added a 5% aqueous solution of polyvinyl alcohol (1.8 parts) as a stabilizer and benzoyl peroxide (0.8 part) as a polymerization initiator. The mixture was heated at about 60°C for 6 hours under a nitrogen atmosphere. After the resulting resin was washed with water and acetone, it was then refluxed with chloroform for 2 hours to wash the resin well.

To a mixture of methanol (1000 parts) and formic acid (500 parts) were added said resin (50 parts) and cupric formate tetrahydrate (60 parts). The resulting heterogeneous mixture was stirred for 24 hours at room temperature and then filtered. The residue was collected and washed with water well until the color of the washing disappeared, thereby producing a coppercontaining polymer catalyst which was, in turn, dried at room temperature under reduced pressure and heated at 200° C for 2 hours under a nitrogen atmosphere to give an activated copper-containing polymer catalyst.

A mixture of the catalyst (15 g) so obtained and a commercially available metallic zinc powder (0.5 g) was charged into a stainless steel reaction tube having a volume of 300 ml and an inner diameter of 10 mm. The reaction tube was connected to a circulation reaction apparatus, and a mixture of acrylonitrile and water in an amount by weight of 1 : 3 was supplied on the catalyst layer at a rate of 65 ml/hr to effect the hydration while keeping the reaction tube at 100° C. At a given interval of time, a part of the reaction mixture was taken and analyzed. The conversion rate was determined by the quantitative analysis by liquid chromatography using dimethylformamide as an inner standard. The determination of the eluted cupric and zinc ions was performed by colorimetry using zincon as an indicator.

The results are shown in Table 1.

Table 1

| Time (hrs.) | Conversion of acrylonitrile (%) | Selectivity to acrylamide (%) | Concentration of eluted cupric ion (ppm) | Concentration of eluted zinc ion (ppm) |
| --- | --- | --- | --- | --- |
| 5 | 78.8 | 99.1 | 1.5 | 1.5 |
| (5) | (78.2) | (99.3) | (40) | (—) |
| 20 | 75.5 | 99.2 | 1.0 | 1.3 |
| (20) | (70.1) | (99.0) | (55) | (—) |
| 50 | 72.4 | 99.1 | 1.0 | 1.2 |
| (50) | (59.3) | (99.1) | (32) | (—) |
| 80 | 68.3 | 99.2 | 0.8 | 1.0 |
| 100 | 65.1 | 99.2 | 0.9 | 1.3 |
| 125 | 64.3 | 99.1 | 0.7 | 1.1 |

Table 1-continued

| Time (hrs.) | Conversion of acrylonitrile (%) | Selectivity to acrylamide (%) | Concentration of eluted cupric ion (ppm) | Concentration of eluted zinc ion (ppm) |
|---|---|---|---|---|
| 150 | 63.8 | 99.2 | 0.8 | 1.2 |

Note: The values enclosed between the parentheses indicate those obtained where no metallic zinc is used.

EXAMPLES 2 – 8

To a suspension of 4-vinylpyridine (80 parts) and divinylbenzene (4.2 parts) in water (320 parts) were added a 5% aqueous solution of polyvinyl alcohol (1.8 parts) as a stabilizer and benzoyl peroxide (0.8 part) as a reaction initiator. The mixture was heated at about 60° C for 6 hours in a nitrogen atmosphere. The resulting mixture was washed with water and with acetone, and refluxed with chloroform for 2 hours to wash the resin well. The yield of the dried product was 90%.

The resin (5 parts) thus obtained was added to a solution of cupric formate tetrahydrate (3 parts) in methanol (200 parts) and formic acid (100 parts) while being stirred vigorously. The resulting heterogeneous mixture was further stirred for 24 hours and then filtered. The residue was washed with water (500 parts) well until the color of the washing disappeared. The copper-containing polymer catalyst so obtained was dried at 80° C and then heated for 2 hours at 200° C.

A nitrile compound (1 part), water (20 parts) and the catalyst (0.1 part) were charged into a 50-ml flask. The hydration was effected in a nitrogen atmosphere. The names of the nitrile compound and the reaction conditions are shown in Table 2 below. After the reaction was completed, the product was recovered by an extraction with a solvent and weighed. The identification of the product was conducted by the infrared absorption spectrum, elementary analysis and mixed examination. The results are shown in Table 2.

Table 2

| Example No. | Reaction temperature (°C) | Reaction time (hrs.) | Starting nitrile compound | Product | Yield (%) | Selectivity (%) |
|---|---|---|---|---|---|---|
| (1) | 85 | 6 | $CH_3CN$ | $CH_3-CONH_2$ | 69 | 100 |
| (2) | 100 | 8 | $NC(CH_2)_4CN$ | $H_2NC-(CH_2)_4-C-NH_2$ (both C=O) | 10 | |
|  |  |  |  | $NC(CH_2)_4-CNH_2$ | 5 | |
| (3) | 100 | 8 |  |  | 80 | 97 |
| (4) | 100 | 6 |  | 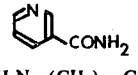 | 50 / 15 | |
| (5) | 85 | 8 | $(CH_3)_2C(OH)CN$ | $(CH_3)_2C(OH)CONH_2$ | 5 | 100 |
| (6) | 100 | 1 | pyridyl-CN | pyridyl-CONH$_2$ | 100 | 100 |
| (7) | 100 | 8 | $H_2N-(CH_2)_5-CN$ | $H_2N-(CH_2)_5-CONH_2$ | 32 | 93 |

EXAMPLE 9

A resin was prepared in the same manner as in Examples 2 to 8 except for using 4-vinylpyridine (40 parts) and styrene (40 parts) in place of 4-vinylpyridine (80 parts).

Using the resulting resin (5 parts) and cupric formate tetrahydrate (6 parts), a copper-containing polymer catalyst was produced by the same procedures as in Examples 2 to 8.

In the presence of the catalyst (0.1 g) thus obtained, the hydration of β-cyanopyridine (1 g) was effected at 100° C for 1 hour in the same manner as in Examples 2 to 8, whereby nicotinamide was given in a 76% yield with a selectivity of 100%.

EXAMPLE 10

To a mixture of copper oxalate hemihydrate (3 parts), methanol (200 parts) and formic acid (100 parts) was added a resin (5 parts) obtained by the same procedures as in Examples 2 to 8 while being stirred vigorously. The resulting mixture was then treated in the same manner as in Examples 2 to 8.

After the catalyst was heated for 2 hours at 200° C, a 10% aqueous solution of cyanic acid (20 parts) and the catalyst (0.1 part) were charged into an autoclave and stirred at 120° C for 5 hours to give formamide. The yield was 73%.

EXAMPLE 11

After the catalyst prepared in the same manner as in Examples 2 to 8 was dried at 80° C, the said catalyst (0.5 part) and a 5% aqueous solution of β-cyanopyridine (15 parts) were charged into an autoclave and stirred for 2 hours at 100°C to give nicotinamide in a yield of 65%.

EXAMPLE 12

As in Examples 2 to 8, a catalyst was prepared from a resin (5 parts) obtained in Examples 2 to 8 and copper tartrate (3 parts).

A 5% aqueous solution of β-cyanopyridine (15 parts) was treated in the same manner as in Example 11 with the catalyst (1 part) to give nicotinamide in a yield of 45%.

EXAMPLE 13

A resin was prepared in the same manner as in Examples 2 to 8 except for using 4-vinylpyridine (20 parts) and styrene (60 parts) in place of 4-vinylpyridine (80 parts). The resulting resin (5 parts) and cupric chloride dihydrate (5 parts) were treated in the same manner as in Examples 2 to 8 to give a catalyst which was, in turn, dried at 80° C and then heated at 200° C for 5 hours in a quartz tube under a hydrogen atmosphere.

Using the catalyst (0.1 part) thus obtained, the same procedures as in Examples 2 to 8 were repeated to give the acetamide in a yield of 35%.

EXAMPLE 14

A catalyst was prepared in the same manner as in Examples 2 to 8 except for the use of 4-vinylpyridine (40 parts) and styrene (40 parts) in place of 4-vinylpyridine (80 parts).

A jacketed stainless steel cylindrical reactor having a diameter of 6 cm and a length of 100 cm was filled with the catalyst (1 kg) and then heated to a specified temperature by means of hot water or steam. A 6% aqueous solution of acrylonitrile was pumped up to the bottom of the reactor with a quantitative pump, and the fluent was collected for 24 hours for the quantitative analysis of acrylamide produced and unreacted acrylonitrile. The reaction conditions and results are shown in Table 3. It is to be noted that hydrates are produced as by-products in an extremely small amount.

Table 3

| Temperature (°C) | Contact time (hrs.) | Conversion of acrylonitrile (%) | Selectivity to acrylamide (%) |
|---|---|---|---|
| 140 | 0.23 | 99.1 | 99.9 |
| 120 | 0.23 | 87.6 | 100.0 |
| 100 | 0.23 | 61.9 | 84.4 |

EXAMPLE 15

Using a resin (5 parts) obtained in Examples 2 to 8 and cupric formate tetrahydrate (6 parts), a copper-containing polymer catalyst was prepared and the hydration of acrylonitrile was effected in the same manner as in Example 14. The results are set out in Table 4.

Table 4

| Temperature (°C) | Contact time (hrs.) | Conversion of acrylonitrile (%) | Selectivity to acrylamide (%) |
|---|---|---|---|
| 80 | 0.11 | 66.4 | 99.3 |
| 90 | 0.11 | 82.4 | 100.0 |
| 90 | 0.06 | 67.0 | 99.0 |
| 100 | 0.11 | 93.7 | 100.0 |

EXAMPLE 16

A polymer was prepared in the same manner as in Examples 2 to 8 except for the use of 4-vinylpyridine (40 parts) and styrene (40 parts) in place of 4-vinylpyridine (80 parts). To the resulting resin (5 parts) was added a mixture of copper oxalate hemihydrate (3 parts) in methanol (200 parts) and formic acid (100 parts) while being stirred vigorously. The mixture was treated in the same manner as in Example 14. After the mixture was then heated for 2 hours at 200° C, the catalyst (1 part) so obtained and a 6% aqueous solution of acrylonitrile (15 parts) were treated in an autoclave for 1 hour at 140° C under 10 atmospheric pressures while being stirred. The quantitative analysis of the reaction mixture showed a 34% conversion of acrylonitrile and a 19.2% selectivity of acrylamide.

EXAMPLE 17

After the catalyst obtained in Example 14 was dried at 80° C, the catalyst (1 part) was reacted with a 6% aqueous solution of acrylonitrile (15 parts) in an autoclave for 1 hour at 140° C under 10 atmospheric pressures while being stirred. The quantitative analysis of the reaction mixture showed an 82.5% conversion of acrylonitrile and a 73.1% selectivity of acrylamide.

EXAMPLE 18

A catalyst was prepared in the same manner as in Examples 2 to 8 except using 4-vinylpyridine (40 parts) and styrene (40 parts) in place of 4-vinylpyridine (80 parts) and copper tartrate (3 parts) in place of cupric formate tetrahydrate (60 parts). The catalyst (1 part) was reacted with a 6% aqueous solution of acrylonitrile (15 parts) in the same manner as in Example 17. The quantitative analysis of the reaction mixture showed a 35.3% conversion of acrylonitrile to acrylamide and a 50.9% selectivity of acrylamide.

EXAMPLE 19

The reaction of the catalyst (1 part) obtained in Example 15 with a 6% aqueous solution of acrylonitrile (15 parts) was carried out using as a polymerization preventing agent, sodium anthraquinone β-sulfonate, under atmospheric pressure for 1 hour at 85° C. The reaction mixture was analyzed quantitatively to show a 68.1% conversion of acrylonitrile and an 86.1% selectivity of acrylamide.

EXAMPLE 20

A polymer was prepared from 4-vinylpyridine (20 parts), styrene (60 parts) and dibenzylbenzene (4.2 parts) in the same manner as in Examples 2 to 8. A catalyst was prepared from the polymer (5 parts) and cupric formate tetrahydrate (3 parts). The catalyst was reacted with acrylonitrile in the same manner as in Example 17 to give a reaction mixture which showed a 45.5% conversion of acrylonitrile and a 74.0% selectivity of acrylamide according to the quantitative analysis.

EXAMPLE 21

The catalyst (0.1 part) obtained in Examples 2 to 8, cyanogen (1 part) and water (10 parts) were treated in an autoclave for 1 hour at 95° C while being stirred, resulting in the production of the oxamide in a yield of 95%.

COMPARATIVE EXAMPLE

A mixture of activated carbon (10 parts) and copper formate (1 part) in methanol (200 parts) and formic acid (100 parts) was stirred for 24 hours. The mixture was then treated in the same manner as in Example 14, and the reaction thereof with acrylonitrile was carried out in the same manner as in Example 17. The reaction mixture showed an 18.3% conversion of acrylonitrile and no formation of acrylamide.

What is claimed is:

1. A process for preparing a carboxylic acid amide by hydrating a nitrile compound with water in the presence of a catalyst comprising a copper-containing polymer obtained (1) by contacting a copper salt or a copper complex having a replaceable ligand with a polymerized material having a basic nitrogenous group in the polymer chain or linked with the polymer chain or (2) by polymerizing a vinyl monomer containing a copper salt or a copper complex having a basic nitrogenous group bonded to the copper atom as a ligand and heat-treating the resulting copper-containing polymer at a temperature of from about 50° to 400°C.

2. The process of claim 1 wherein the hydration reaction is carried out at a temperature of from about 10° to 300° C.

3. The process of claim 1 wherein the hydration reaction is carried out at a temperature of from about 10° to 200° C.

4. The process of claim 1 wherein the hydration reaction is carried out with the use of water in an amount from about 1.5 to 50 times more than the stoichiometric amount of the nitrile compound used.

5. The process of claim 1 wherein the hydration reaction is carried out in the liquid phase.

6. The process of claim 1 wherein the hydration reaction is carried out in a suspension procedure or a fixed bed procedure.

7. The process of claim 1 wherein the polymerized material is a homopolymer of 2-vinylpyridine, 4-vinylpyridine, 2-methyl-4-vinylpyridine, 2-butyl-4-vinylpyridine, N,N-diethylaminomethylmethacrylate, N,N-diethylaminoethylmethacrylate, N,N-dimethylaminoethylacrylate, N,N-dimethylaminoethylmethacrylate or vinylisoquinoline or a copolymer thereof with styrene, vinyltoluene or a cross-linking agent selected from the group consisting of divinylbenzene, divinylphthalate and ethylene glycol diacrylate.

8. The process of claim 1 wherein the nitrile compound is acetonitrile, propionitrile, butyronitrile, methoxyacetonitrile, acrylonitrile, methacrylonitrile, ethacrylonitrile, crotononitrile, α-chloroacrylonitrile, α-bromoacrylonitrile, cyclopentanonitrile, cyclohexanecarbonitrile, benzyl cyanide, cinnamonitrile, α-naphthylacetonitrile, benzonitrile, naphthonitrile, nicotinonitrile, oxalonitrile, malononitrile, succinonitrile, glutaronitrile, adiponitrile, pimelonitrile, suberonitrile, sebaconitrile, maleonitrile, cyclobutane 1,2-dicyanide, phthalonitrile, benzoyl cyanide or acetyl cyanide.

9. The process of claim 1 wherein the hydration reaction is carried out by adding to the reaction system metallic zinc in an amount of from about 0.001 to 200% by weight of the copper-containing polymer catalyst.

10. The process of claim 1 wherein the copper salt is a copper salt of an inorganic acid selected from the group consisting of copper chloride, copper bromide, copper sulfate and copper nitrate.

11. The process of claim 1 wherein the copper salt is a copper salt of an organic acid selected from the group consisting of copper formate, copper acetate, copper oxalate and copper tartrate.

12. A process for preparing a carboxylic acid amide by hydrating a nitrile compound with water in an amount of from about 1.5 to 50 times more than the stoichiometric amount of the nitrile compound at a temperature of from about 10° to 300°C. in the presence of a copper-containing polymer catalyst obtained by contacting a copper salt or a copper complex having a replaceable ligand with a polymerized material having a pyridine ring in the polymer chain or linked with the polymer chain and heat-treating the resulting copper-containing polymer at a temperature of from about 50° to 400°C.

13. The process of claim 12 wherein said copper salt is a salt of an organic acid.

14. The process of claim 13 wherein said copper salt is copper formate.

15. The process of claim 12 wherein said copper complex is a copper complex containing a basic nitrogenous group.

16. The process of claim 12 wherein said polymerized material is poly(2-vinylpyridine), poly(4-vinylpyridine), styrene-2-vinylpyridine copolymer or styrene-4-vinylpyridine copolymer.

17. The process of claim 12 wherein said polymerized material is cross-linked with divinylbenzene.

* * * * *